(12) United States Patent
Serrano (10) Patent No.: US 7,526,849 B2
(45) Date of Patent: May 5, 2009

(54) STENT LOADER

(75) Inventor: Gabriel Sobrino Serrano, Kinvara (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 664 days.

(21) Appl. No.: 11/245,521

(22) Filed: Oct. 7, 2005

(65) Prior Publication Data
US 2007/0079494 A1    Apr. 12, 2007

(51) Int. Cl.
A61F 2/06 (2006.01)
B23P 11/02 (2006.01)
B23P 19/04 (2006.01)

(52) U.S. Cl. ............... 29/508; 29/252; 29/505; 29/507; 623/1.12; 623/1.23

(58) Field of Classification Search ............ 29/252, 29/505, 507, 508, 715; 623/1.12, 1.23
See application file for complete search history.

(56) References Cited

U.S. PATENT DOCUMENTS

| | | | |
|---|---|---|---|
| 5,746,764 A | 5/1998 | Green et al. | 606/194 |
| 5,911,452 A | 6/1999 | Yan | 29/516 |
| 5,928,258 A | 7/1999 | Khan et al. | 606/191 |
| 6,009,614 A * | 1/2000 | Morales | 29/516 |
| 6,132,458 A | 10/2000 | Staehle et al. | 623/1.11 |
| 6,241,758 B1 | 6/2001 | Cox | 623/1.11 |
| 6,322,586 B1 | 11/2001 | Monroe et al. | 623/1.11 |
| 6,360,577 B2 | 3/2002 | Austin | 72/402 |
| 6,471,718 B1 | 10/2002 | Staehle et al. | 623/1.11 |
| 6,607,551 B1 | 8/2003 | Sullivan et al. | 623/1.11 |
| 6,613,075 B1 | 9/2003 | Healy et al. | 623/1.11 |
| 6,745,445 B2 | 6/2004 | Spilka | 29/407.08 |
| 6,823,576 B2 | 11/2004 | Austin | 29/516 |
| 6,858,034 B1 | 2/2005 | Hijlkema et al. | 606/108 |
| 6,859,986 B2 | 3/2005 | Jackson et al. | 29/458 |
| 6,863,683 B2 | 3/2005 | Schwager et al. | 623/1.11 |

(Continued)

FOREIGN PATENT DOCUMENTS

WO    WO 2005/070335 A1    8/2005

OTHER PUBLICATIONS

U.S. Appl. No. 11/087,411, filed Mar. 23, 2005, Serrano et al.

*Primary Examiner*—David P Bryant
*Assistant Examiner*—Alexander P Taousakis
(74) *Attorney, Agent, or Firm*—Vidas, Arrett & Steinkraus, P.A.

(57) ABSTRACT

A stent loading device may comprise a stent crimping device, a fluid source and a support device arranged to support and move a stent delivery device. The fluid source may provide chilled fluid capable of placing a shape memory material into a martensitic state. After stent crimping, as the crimping device opens, the fluid flow may advance at least a portion of the stent into the delivery device. A step procedure may be used to move the rest of the stent into the delivery device, wherein the delivery device may be moved away from the crimping device, the portion of the stent still in the crimping device may be crimped again, and the delivery device may be moved back to its original position, thereby stepping another portion of the stent into the delivery device. The step procedure may be repeated until the entire stent is oriented within the delivery device.

17 Claims, 8 Drawing Sheets

U.S. PATENT DOCUMENTS

| | | |
|---|---|---|
| 6,915,560 B2 | 7/2005 | Austin .......................... 29/722 |
| 6,948,223 B2 | 9/2005 | Shortt |
| 7,010,850 B2 * | 3/2006 | Hijlkema et al. .............. 29/702 |
| 7,448,122 B1 * | 11/2008 | Kokish et al. ................. 29/450 |
| 2002/0035774 A1 | 3/2002 | Austin .......................... 29/516 |
| 2002/0177899 A1 | 11/2002 | Eum et al. ................. 623/23.7 |
| 2002/0193863 A1 | 12/2002 | Rourke et al. .............. 623/1.11 |
| 2003/0192164 A1 | 10/2003 | Austin .......................... 29/505 |
| 2003/0208254 A1 | 11/2003 | Shortt ...................... 623/1.11 |
| 2004/0148000 A1 | 7/2004 | Bilge ........................ 623/1.11 |
| 2004/0148007 A1 | 7/2004 | Jackson et al. ............. 623/1.12 |
| 2004/0199239 A1 | 10/2004 | Austin et al. ............... 623/1.11 |
| 2005/0119720 A1 | 6/2005 | Gale et al. ................. 623/1.11 |
| 2005/0154450 A1 | 7/2005 | Larson et al. ............. 623/1.42 |
| 2005/0166389 A1 | 8/2005 | Perreault et al. .............. 29/508 |
| 2005/0183259 A1 | 8/2005 | Eidenschink et al. .......... 29/508 |
| 2005/0188525 A1 | 9/2005 | Weber et al. ................. 29/508 |
| 2005/0229670 A1 | 10/2005 | Perreault .................... 72/402 |
| 2005/0234537 A1 | 10/2005 | Edin ........................ 623/1.11 |

* cited by examiner

STENT LOADER

FIELD OF THE INVENTION

In some embodiments this invention relates to implantable medical devices, their manufacture, and methods of use. Some embodiments are directed to delivery systems, such as catheter systems of all types, which are utilized in the delivery of such devices.

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents and similar devices such as grafts, stent-grafts, expandable frameworks, and similar implantable medical devices, are radially expandable endoprostheses that are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Stents, such as self-expanding stents, can be loaded into delivery catheters by pushing the stent through a funnel, as disclosed in U.S. Pat. No. 6,471,718, or by pushing a crimped stent out of a crimping device, for example as disclosed in U.S. Pat. No. 6,360,577, and into a catheter. The disclosures of U.S. Pat. No. 6,471,718 and U.S. Pat. No. 6,360,577 are hereby incorporated herein by reference in their entireties.

In some embodiments, stents may include coatings, such as lubricious coatings and/or drug coatings. The presence of a coating may complicate procedures for reducing the size of a stent and loading the stent into a delivery system, especially when the stent is relatively long and/or when the stent is self-expanding. Sliding friction between the crimping device and the stent or coating may cause damage to the stent, coating and/or the crimping device.

There remains a need for inventive methods and devices for loading stents into a stent delivery system.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the invention is directed to a method of loading a self-expanding stent which includes providing a crimping device having a crimping chamber constructed and arranged to reduce the diameter of a stent. A support device is be provided to support a delivery device having an internal diameter. The support device is constructed and arranged to move the delivery device with respect to the crimping device, and the delivery device is oriented to receive a stent from said crimping device. A fluid source is provided and arranged to direct a fluid flow through the crimping chamber of the crimping device. The fluid is provided at a temperature lower than an ambient temperature and is desirably capable of placing a shape memory material into a martensitic state. A self-expanding stent is provided and oriented within the crimping chamber of the crimping device. Fluid flow is directed through the crimping chamber of the crimping device. The size of the crimping chamber is reduced to reduce an outer diameter of the stent to less than the internal diameter of the delivery device. The size of the crimping chamber is increased, wherein said fluid flow advances the stent such that at least a portion of the stent exits the crimping chamber and enters the delivery device. A step procedure is performed wherein the delivery device is moved away from the crimping device, thereby moving another portion of the stent out of the crimping chamber. The size of the crimping chamber is again reduced to reduce the portion of the stent oriented within the crimping chamber to an outer diameter less than the internal diameter of the delivery device. The delivery device is moved back toward the crimping device, thereby further advancing the stent into the sheath. In the event that a portion of the stent is still oriented within the crimping chamber, the size of the crimping chamber may again be increased, and the step procedure may be repeated as necessary until the entire stent is oriented within the sheath.

In at least one other embodiment, the invention is directed to a system for loading a self-expanding stent comprising a crimping device, a support device and a fluid source. The crimping device includes a crimping chamber constructed and arranged to reduce the diameter of a stent. The support device is constructed and arranged to support a stent delivery device and to move the delivery device in at least two axial directions with respect to the crimping chamber. The stent delivery device has a longitudinal axis and an internal diameter, is coaxially aligned with an axis of the crimping chamber and is oriented to receive a stent from said crimping device. The fluid source is arranged to direct a fluid flow through the crimping chamber of the crimping device, the fluid being at a temperature capable of placing a self-expanding stent into a martensitic state. When a self-expanding stent is oriented within the crimping chamber in a martensitic state such that an outer diameter of the stent is less than the internal diameter of the stent delivery device, and the size of the crimping chamber is increased, the fluid flow advances the stent such that at least a portion of the stent exits the crimping chamber and enters the stent delivery device.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
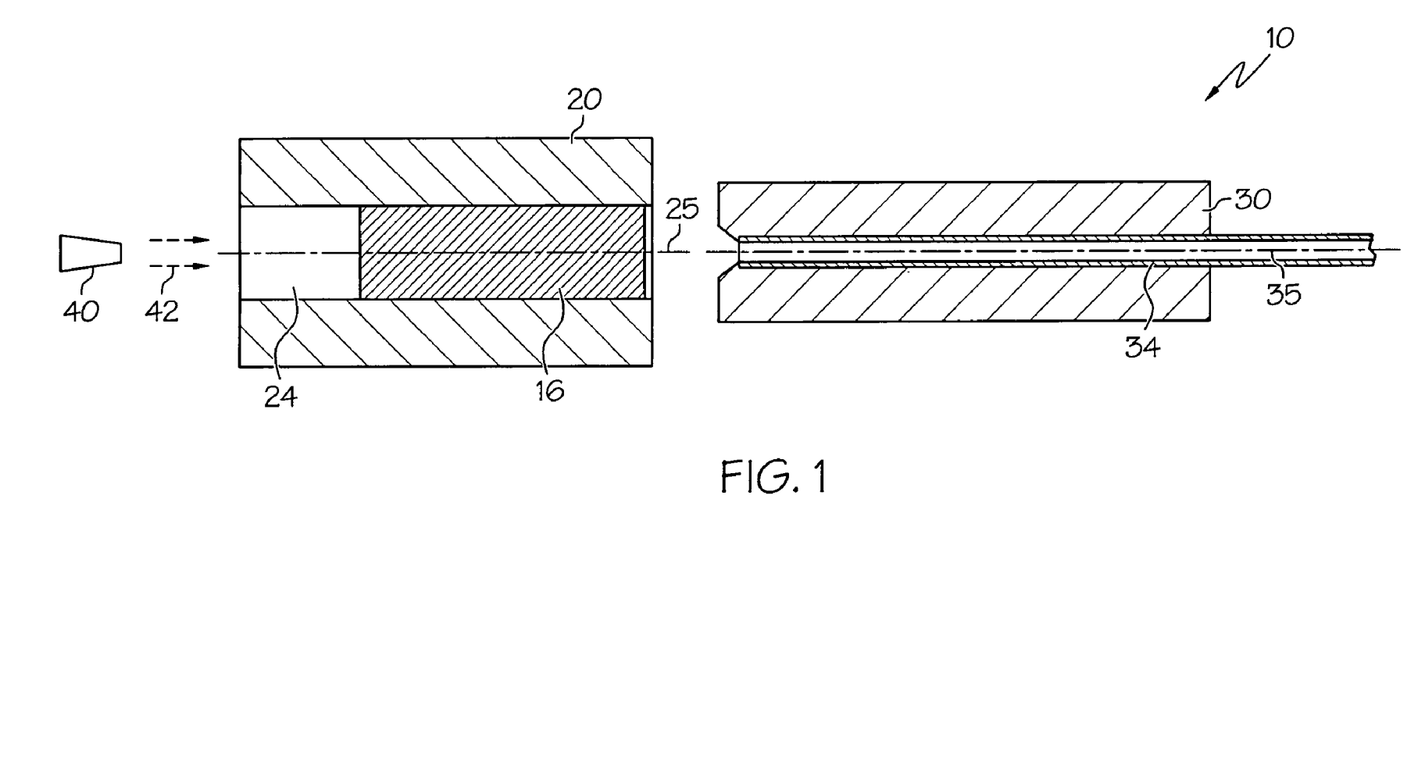
FIGS. 1-8 show an embodiment of a stent loading device during various stages of a stent crimping and loading process.

FIG. 1 shows an embodiment of a loading device 10 suitable for loading a stent 16 into a stent delivery device 34. The loading device 10 may comprise a crimping device 20, a fluid supply 40 and a support device 30 arranged to support a stent delivery system.

A crimping device 20 may comprise any device suitable for reducing the size or diameter of a stent 16 or other expandable medical device. In some embodiments, a crimping device 20 may comprise an iris crimping mechanism and may have a plurality of coupled movable dies 22 arranged to form a crimping chamber 24 of variable size. A stent 16 may be placed within the crimping chamber 24, and the size of the stent 16 may be reduced as the size of the crimping chamber 24 is reduced during a crimping procedure. Some examples of crimping devices that may be suitable for use in a loading device 10 are disclosed in U.S. Pat. Nos. 6,360,577, 6,823, 576 and 6,915,560, and U.S. patent application Ser. Nos. 10/784,337, 10/767,985, 10/788,088, 10/826,035, 10/826, 196 and 11/087,411, the entire disclosures of which are hereby incorporated herein in their entireties.

The crimping chamber 24 may include a central longitudinal axis 25. When a stent 16 is placed within the crimping chamber 24, an axis of the stent may be centered along the central longitudinal axis 25.

A support device 30 is desirably arranged to support at least a portion of a stent delivery device 34, such as a catheter, sheath or the like. The support device 30 may orient a stent delivery device 34 to receive a stent from the crimping chamber 24 of the crimping device 20. In some embodiments, a central longitudinal axis 35 of the stent delivery device 34 may be aligned with the axis 25 of the crimping chamber 24, and with the axis of the stent 16. The support device 30 is desirably arranged to move the stent delivery device 34 with respect to the crimping chamber 24. In some embodiments, the support device 30 may be arranged to move the stent delivery device 34 back and forth in an axial direction while keeping the axis 35 of the catheter 34 aligned with the axis 25 of the crimping chamber 24. The back and forth movement of the delivery device 34 may be used in conjunction with relatively small opening and closing movements of the crimping device 20 in a repeating step operation to step portions of the stent 16 out of the crimping chamber 24 and into the delivery device 34, as described in detail below.

A fluid supply 40 may be arranged to direct fluid flow 42 through the crimping chamber 24. In some embodiments, fluid flow 42 may continue through the support device 30 and through the stent delivery device 34.

In some embodiments, at least a portion of the fluid flow 42 may help to move the stent 16, in a crimped or reduced configuration, out of the crimping chamber 24 and into/onto the stent delivery device 34. In addition to mechanically pushing the stent 16 out of the crimping chamber 24, a portion of the fluid flow 42 may also act as a lubricant or cushion between the stent 16 and the interior contacting surfaces of the crimping device 20.

Fluid provided by the fluid supply 40 may have a different temperature than the ambient temperature, and may be used to adjust the temperature of the stent 16, the crimping device 20, the support device 30 and the stent delivery device 34. In some embodiments, the fluid flow 42 may be cooler than the ambient temperature. In some embodiments when loading a self-expanding stent 16, the fluid flow 42 may have a temperature low enough to cool the stent 16 to a martensitic state. In some embodiments when loading a stent 16 having a drug coating or other type of coating, the fluid flow 42 may have a temperature low enough to cool the coating to a level that it becomes less susceptible to being stripped, marred or otherwise damaged as the stent 16 is ejected from the crimping chamber 24. For example, a coating may be cooled to a level below a glass transition temperature of the coating, wherein portions of the coating may harden or solidify. A coating that is maintained at a low temperature, for example below the glass transition temperature, may contribute to keeping the stent 16 at a crimped or reduced diameter during the loading operation. In some embodiments, various coatings may have glass transition temperatures in the range of −30 degrees C. to −50 degrees C. Some examples of fluid temperature that may be provided range from ambient room temperature to temperatures lower than −90 degrees C, and in some embodiments even lower than −196 degrees C.

The fluid supply 40 may provide any suitable type of fluid that is desirably capable of moving and/or imparting a temperature change to the stent 16. In some embodiments, the fluid may comprise a gas, such as air, and desirably an inert gas, such as nitrogen. In some embodiment, the use of dry gasses helps to minimize the formation of condensation in the loading equipment.

In some embodiments, the fluid may comprise a liquid. In some embodiments, liquid nitrogen may be used, which may be supplied at temperatures of −196 degrees C. or less.

Fluid may be provided at any suitable pressure and may be arranged to flow at any suitable velocity. When the fluid comprises gas, pressures of 0-12 psi are generally suitable. In some embodiments, a volume ranging from 50-280 liters of gas may pass through the loading device every minute.

Various embodiments of a loading device 10 may be used to load various embodiments of stents 16 into/onto various embodiments of stent delivery devices 34. For example, a balloon expandable stent may be loaded onto a balloon catheter. A self-expanding stent may be loaded into a restraining sheath or catheter shaft.

Some embodiments of a loading device 10 may be particularly useful for loading self-expanding, drug coated stents into restraining sheaths. An embodiment of a method for crimping and loading a stent using an embodiment of a loading device 10 will be described with particular respect to a self-expanding, coated stent 16.

The crimping chamber 24 of the crimping device 20 may be opened to a size suitable for receiving a stent 16 in a nominal or expanded state, and the stent 16 may be placed inside the crimping chamber 24. The size of the crimping chamber 24 may be slightly reduced such that the internal surfaces of the crimping chamber 24 contact and engage the stent 16. In some embodiments, the stent 16 may be pre-crimped to any desirable size.

Fluid flow 42 from the fluid supply 40 may be provided as desired during any stage of the crimping and loading process. In some embodiments, fluid flow 42 may be provided continuously throughout the entire crimping and loading process. In some embodiments, fluid flow 42 may begin when the crimping device 20 engages the stent 16, thereby preventing the fluid flow 42 from ejecting the stent 16 from the crimping chamber 24.

The fluid flow 42 may be provided at a temperature lower than an ambient temperature. In some embodiments, the temperature may be low enough to place the self-expanding stent 16 into a martensitic state. A low temperature may further cool any coating on the stent 16, making the coating more resistant to surface damage. Desirably the stent 16 may be cooled by the fluid flow 42 to a martensitic state. In some embodiments, the stent 16 may be cooled to a temperature that is less than the martensitic start ($M_s$) temperature for the shape memory material of the stent 16, and in some embodiments the stent 16 may be further cooled to a temperature that is less than the martensitic finish ($M_f$) temperature. In embodiments where the stent 16 comprises Nitinol, the stent 16 may be maintained within a temperature range of −60 degrees C. to −90 degrees C. or less. In some embodiments, maintaining the temperature of a Nitinol stent at or below approximately −86 degrees C. may guarantee a full martensitic phase transformation.

Figures 2, 2A:
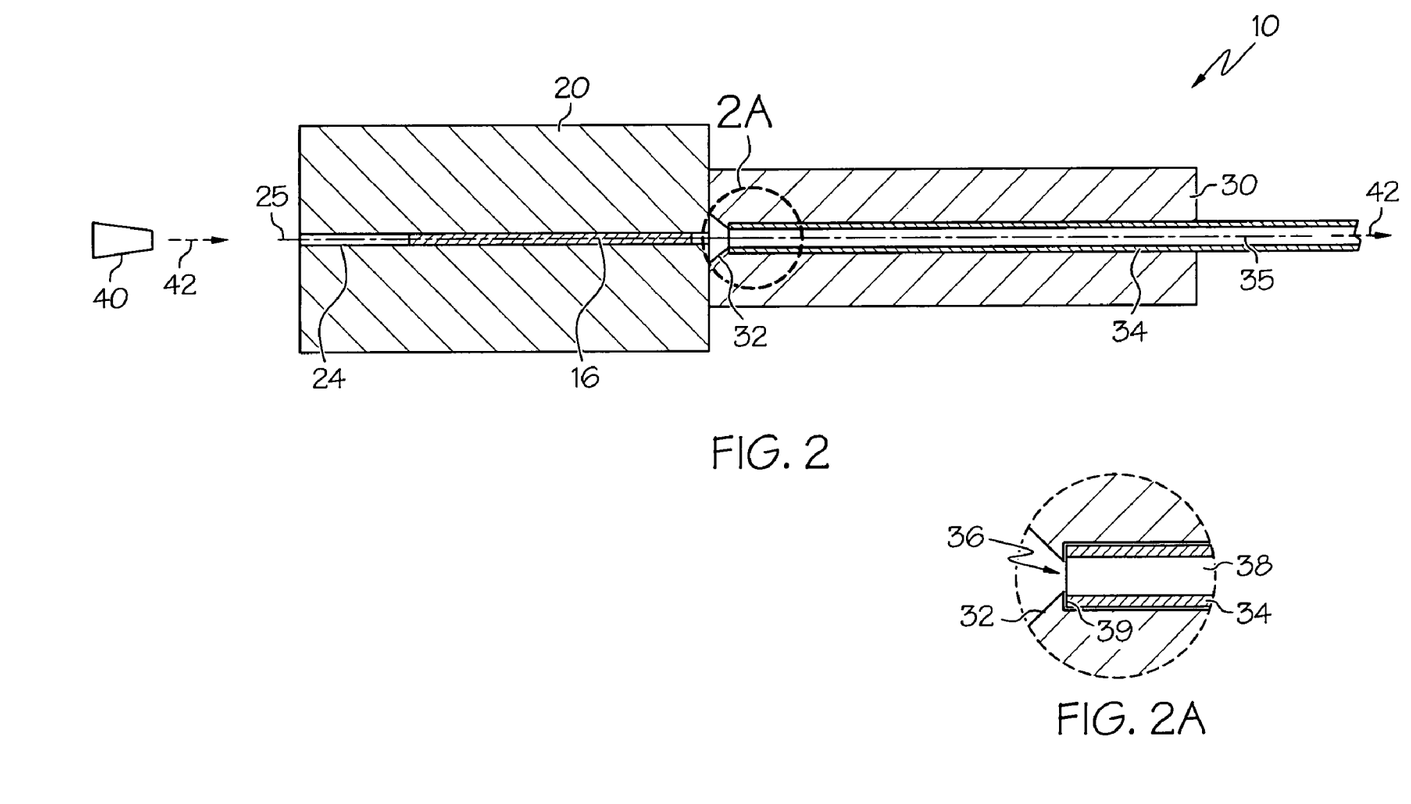

Referring to FIG. 2, the size of the crimping chamber 24 may be reduced, thereby crimping the stent 16. The delivery device 34 may be oriented adjacent to the crimping chamber 24 and arranged to receive the stent 16 from the crimping chamber 24. The longitudinal axis 35 of the delivery system 34 may be aligned with the longitudinal axis 25 of the crimping chamber 24. In some embodiments, the support device 30 may abut the crimping device 20.

Fluid flow 42 from the fluid supply 40 may pass through the crimping chamber 24, the stent 16, the support device 30 and the delivery system 34. In some embodiments, the delivery system 34 may be cooled to the temperature of the fluid flow 42.

The stent 16 may be crimped to a fully crimped state having a fully crimped size or diameter. An outer diameter of the stent 16 in the fully crimped state is desirably less than an inner diameter of the delivery system 34.

In some embodiments, the support device 30 may comprise a shaped end portion 32 arranged to guide the stent 16 into the delivery system 34. For example, the shaped end portion 32 may include a frustoconical shape having an opening 36 through which the stent 16 may pass. The support device 30 may further include an interior cavity 38 arranged to receive the delivery device 34. When positioned within the support device 30, an end of the delivery device 34 may abut a flange 39 adjacent to the opening 36. Desirably, an inner diameter of the delivery device 34 may be equal to or greater than the diameter of the opening 36.

Figure 3:
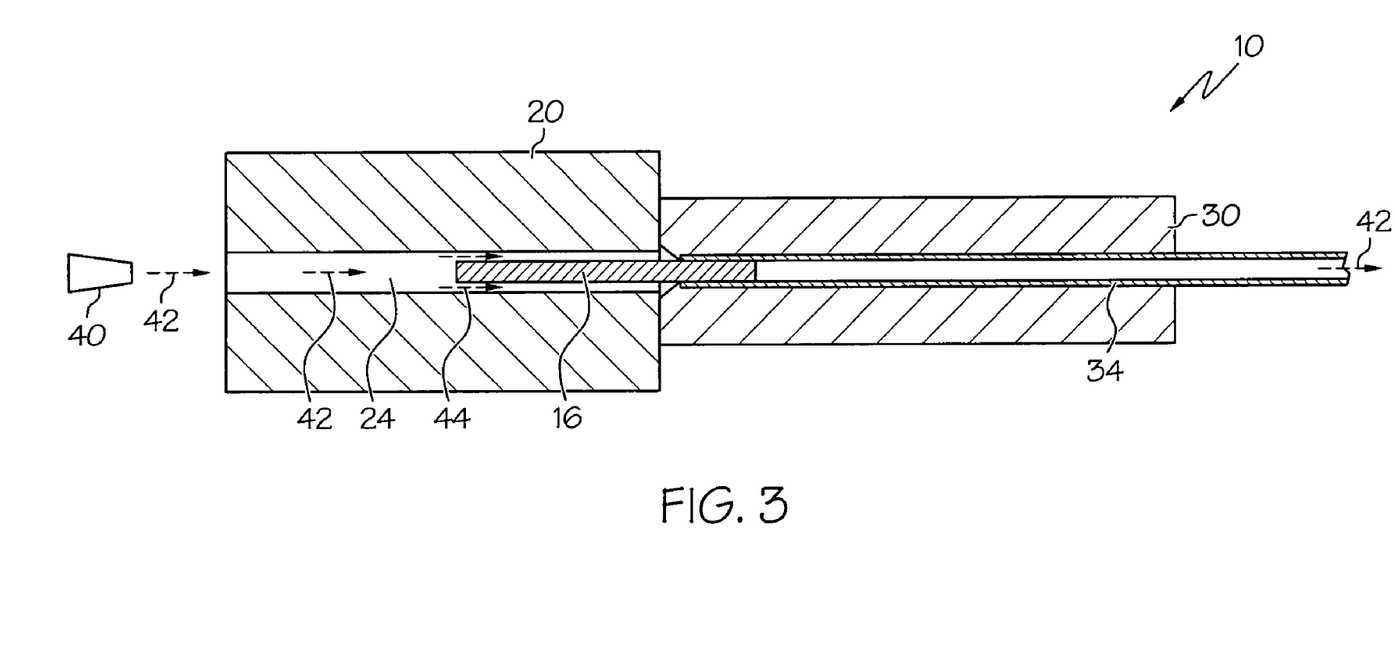

The size of the crimping chamber 24 may be increased to an intermediate size, as shown in FIG. 3. Desirably, the stent 16 is in a martensitic state and will retain the fully crimped configuration for at least a period of time long enough for the fluid flow 42 to advance the stent 16 such that at least a portion of the stent 16 exits the crimping chamber 24 and enters the delivery device 34. The portion of the stent 16 which exits the crimping chamber 24 may be less than the full length of the stent 16.

In addition to advancing the stent 16, the fluid flow 42 may also act as a fluid cushion 44 between the stent 16 and the walls of the crimping chamber 24, thereby reducing frictional forces that could hinder stent advancement and/or damage coatings provided on the stent 16. In some embodiments, the fluid flow 42 may advance the stent 16 until a portion of the stent 16 expands sufficiently to create friction between the stent 16 and the delivery device 34.

In some embodiments, a self-expanding stent 16 may begin to expand immediately upon the increase in size of the crimping chamber 24. Desirably, the crimping chamber 24 may open faster than the stent 16 is capable of expanding, thereby allowing some advancement of the stent 16 before friction between the stent 16 and the delivery device 34 hinders advancement.

In some embodiments, a mechanical advancement device (not shown) may be used to initially move the stent 16 from the crimping chamber 24. For example, a pusher device or mandrel may be arranged to pass through a portion of the crimping chamber 24, contact an end of the stent 16 and begin stent advancement. A mechanical advancement device may be used in any embodiment and may be particularly desirable in embodiments where the fluid flow 42 is not capable of advancing the stent 16, and in embodiments of the invention where fluid flow 42 is not used.

Figure 4:
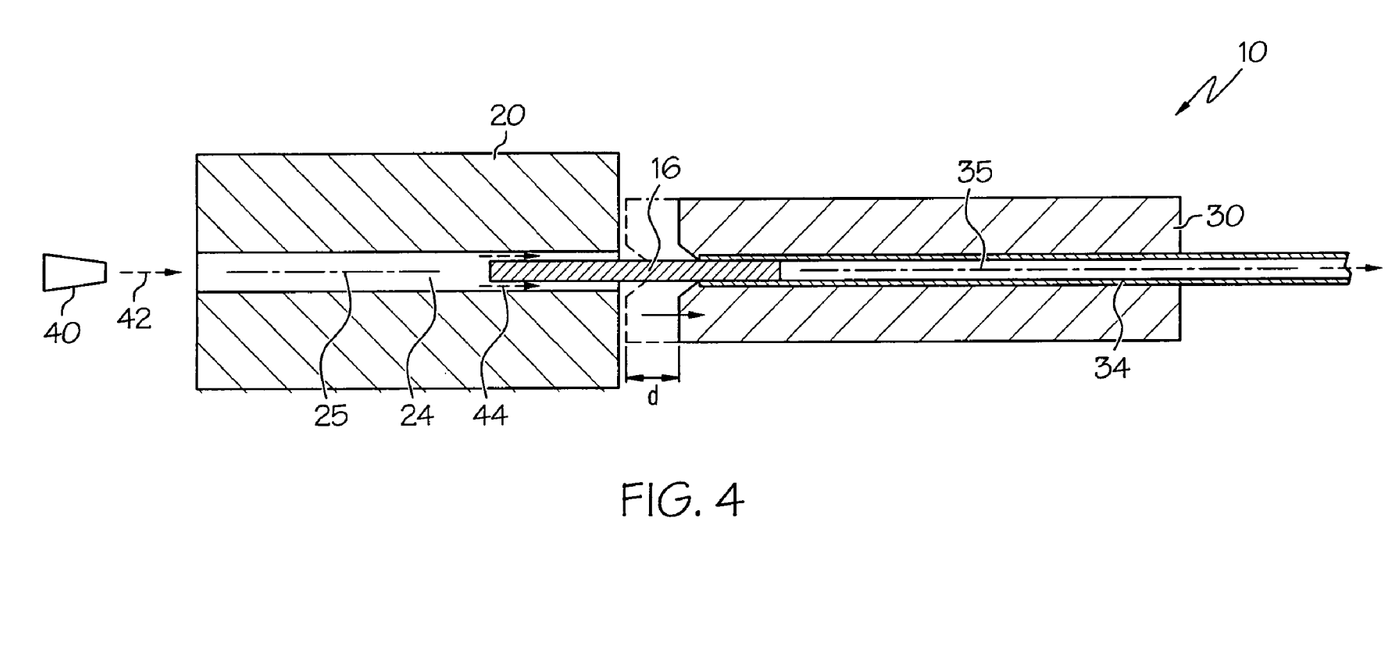

When advancement of the stent 16 due to fluid flow 42 has stopped, the delivery device 34 may be moved away from the crimping device 20, as shown in FIG. 4. In some embodiments, the support device 30 may move with the delivery device 34. Desirably, the delivery device 34 may be moved in an axial direction and the axis 35 of the delivery device 34 may remain aligned with the axis 25 of the crimping chamber 24. The stent 16 may move with the delivery device 34, and another portion of the stent 16 may exit the crimping chamber 24. In some embodiments, fluid flow 42 may continue to provide a fluid cushion 44 between the stent 16 and the crimping chamber 24.

The delivery device 34 may be moved any suitable distance d with respect to the crimping chamber 24. In various embodiments, each displacement of the delivery system 34 may comprise a movement of distance d ranging from less than 1 mm to greater than 10 mm, or any suitable amount in between. In some embodiments, steps of 2.5 mm and/or 5 mm may be used.

Figure 5:
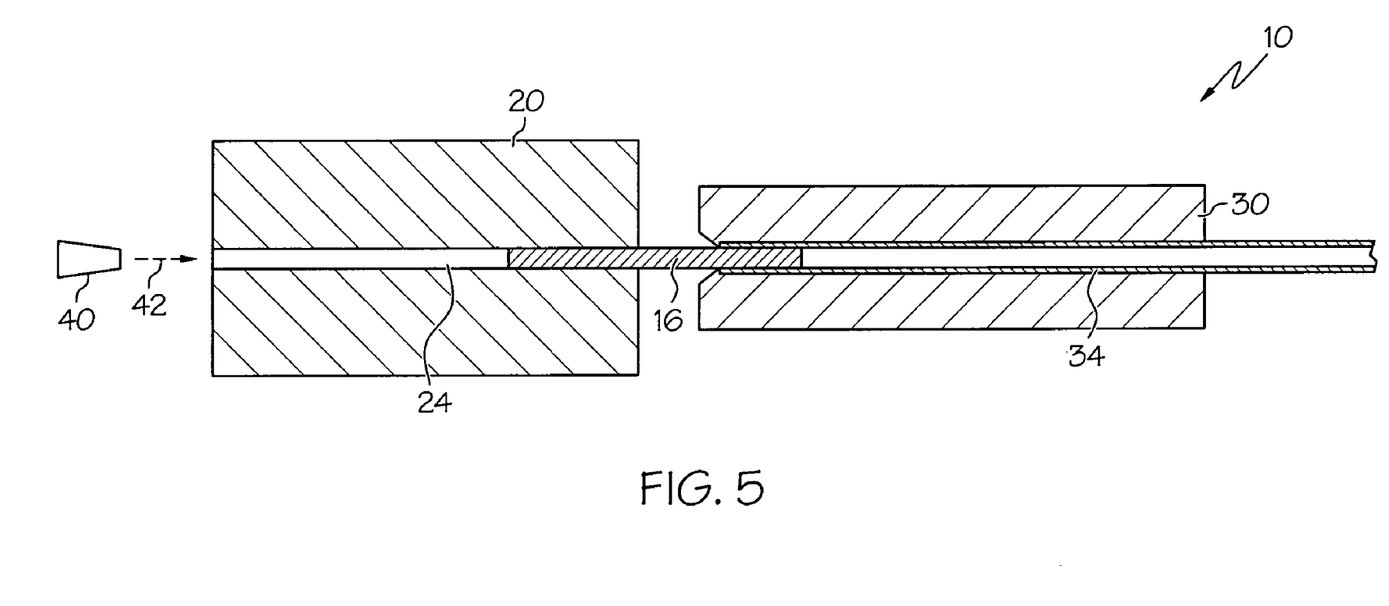

After the delivery device 34 has moved the full distance d, the size of the crimping chamber 24 may again be reduced to fully crimp the portion of the stent 16 still oriented within the crimping chamber 24, as shown in FIG. 5.

Figure 6:
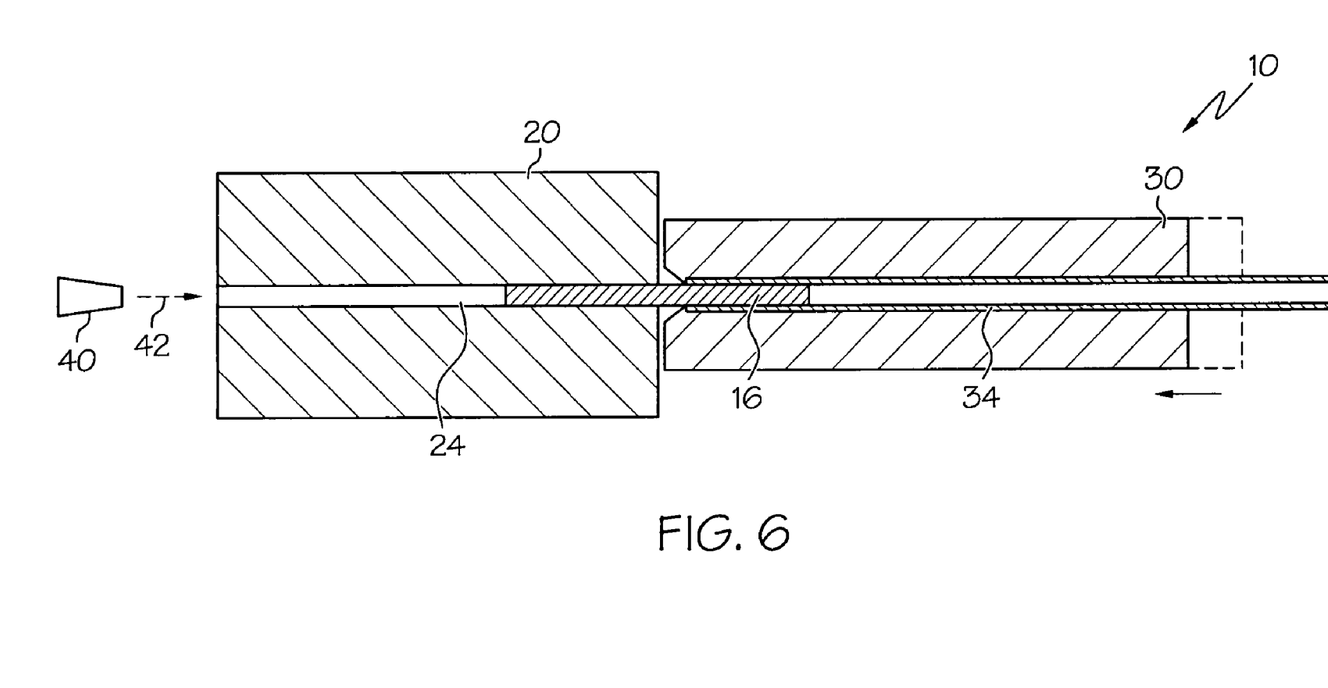

The delivery device 34 may be moved back toward the crimping chamber 24, as shown in FIG. 6. Friction between the stent 16 and the crimping chamber 24, as well as any forces imparted on the stent 16 from the fluid flow 42, desirably prevent the stent 16 from moving with respect to the crimping device 20. As the delivery device 34 is moved toward the crimping chamber 24, the stent 16 may move within the delivery device 34, and a greater portion of the stent 16 may become oriented within the delivery device 34. Fluid flow 42 desirably keeps the stent 16 and delivery device 34 at substantially the same temperature, which may be relatively low and may facilitate movement of the stent 16 and lower the risk of damage to any coating provided on the stent 16.

Figure 7:
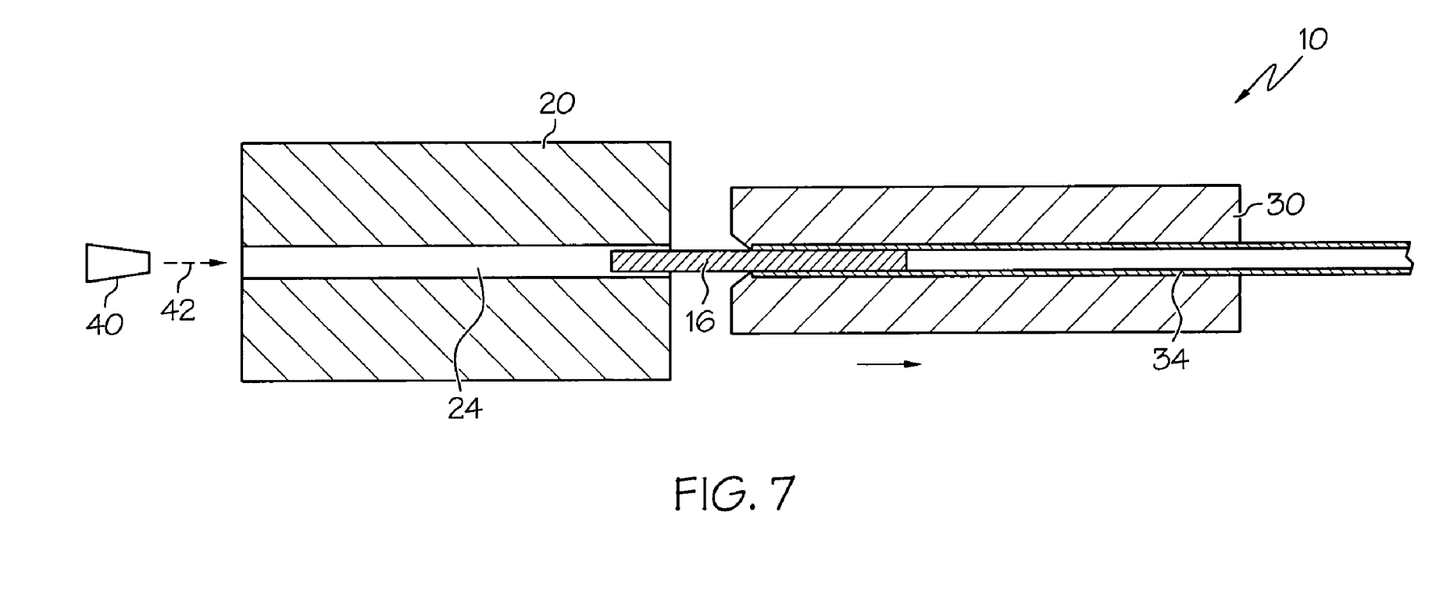

As shown in FIG. 7, the crimping chamber 24 may again be increased to an intermediate size, and the delivery device 34 may again be moved away from the crimping chamber 24. The stent 16 may move with the delivery device 34 and another portion of the stent 16 may exit the crimping chamber 24.

Figure 8:
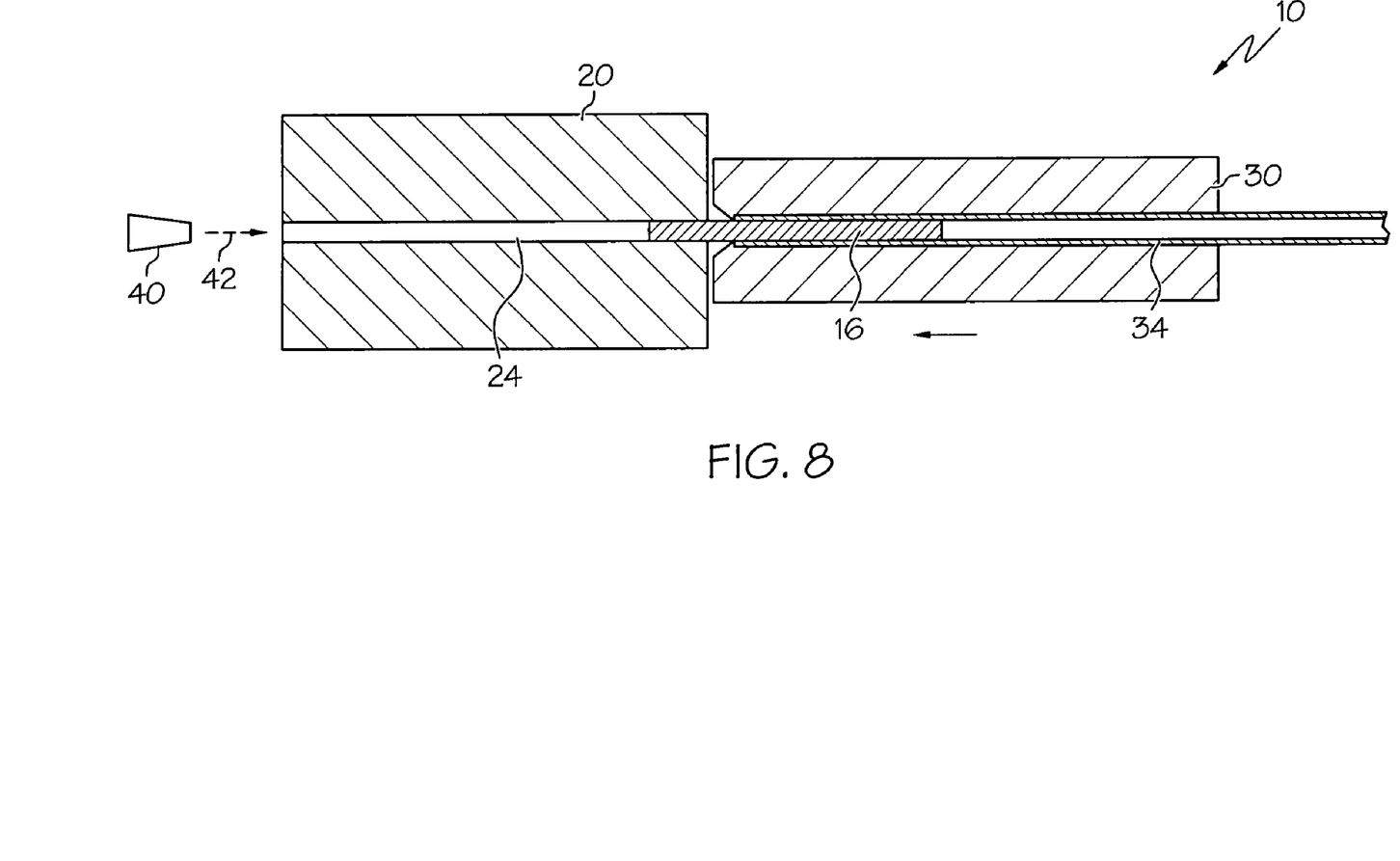

The size of the crimping chamber 24 may again be reduced to fully crimp the portion of the stent 16 still oriented within the crimping chamber 24, as shown in FIG. 8. The delivery device 34 may again be moved back towards the crimping chamber 24, thereby advancing another portion of the stent 16 into the delivery device 34.

In some embodiments, the operations of increasing the size of the crimping chamber 24; moving the delivery device 34 away from the crimping chamber 24, thereby moving another portion of the stent 16 out of the crimping chamber 24; reducing the size of the crimping chamber 24; and moving the delivery device 34 toward the crimping chamber 24, thereby further advancing the stent 16 into the delivery device 34, may comprise a step operation. The step operation may be repeated until the full length of the stent 16 is oriented within the delivery device 34.

During step operations, the delivery system 34 may be moved any suitable distance d (see FIG. 4) with respect to the crimping chamber 24. In some embodiments, the amount of displacement may remain the same between successive step operations. In some embodiments, the amount of displacement may be adjusted between successive step operations.

It should also be noted that many factors influence the amount that the stent 16 moves with respect to the crimping chamber 24 and the delivery device 34 during step operations. Although many parameters may remain the same between successive step operations, the amount of actual stent 16 advancement may vary. Therefore, one stent crimping and loading operation may require four step operations, while a second stent crimping and loading operation six step operations, even though parameters such as stent size, fluid temperature, fluid pressure, etc., may remain the same between operations.

In some embodiments, the crimping device 20 may be cooled by means other than the fluid flow 42. Any suitable method for cooling a crimping device 20 and a stent 16 oriented therein may be used in a loading device 10. For example, dies of the crimping device 20 which contact the stent 16 may be cooled and may remove heat from the stent 16. Cooling can be accomplished using liquid nitrogen or any other suitable method.

In some embodiments, a stent 16 may be provided at a low temperature. For example, a stent 16 may be chilled to a martensitic state prior to being inserted into the crimping chamber 24.

Embodiments of the loading device 10 may work particularly well for loading stents that are relatively long, for example 90 mm, 100 mm, 120 mm or more.

Embodiments of the loading device 10 may work particularly well for loading stents that have coatings which may be susceptible to surface damage.

Embodiments of the loading device 10 may allow for minimal friction between the stent 16 and the walls of the crimping chamber 24, minimizing wearing of the dies and the possibility of carrying die material into the delivery device 34. Embodiments of the loading device 10 may allow for minimal friction between any coating provided on the stent 16 and the walls of the crimping chamber 24, preserving the integrity and properties of the coating.

TESTING AND VARIABLES

In testing, various embodiments of a stent loader 10 were used to load self-expanding stents of differing sizes into delivery devices.

A loading procedure includes many parameters that may be adjusted, such as temperature of the crimping blades, crimp velocity, fire size (size across the crimping chamber during the first crimping step in the loading cycle), crimping force supplied by the crimper actuator, diameter of the stent during an initial chilling, length of the initial chilling, iris chilling size (size of the crimping chamber as chilling fluid flows during intermediate steps of the loading process), step speed and distance, pressure and velocity of fluid flow, crimp diameter, etc.

EXAMPLE 1

Twelve examples of self-expanding stents of size 10×103 mm were successfully loaded into delivery devices under the following conditions.

| Settings for Experiment | |
|---|---|
| Crimp Velocity = | 32.8 mm/sec |
| Fire Size = | 1.6 mm |
| Crimp Force = | 70 Lbs |
| Stent Chill Size = | 10 mm |
| E-Tube chilling time = | 2 sec |
| Iris Chilling size = | 1.8 mm |
| E-Tube Diameter = | 6 French |
| Step Distance = | 5 mm |

| Stent | Number of Crimps | Average Temperature (degrees C.) | Loading Air Pressure (psi) | Stent Length When Loaded (mm) |
|---|---|---|---|---|
| 1 | 5 | −18 | 10.49 | 106.5 |
| 2 | 4 | −19 | 10.49 | Pass through |
| 3 | 4 | −17 | 10.49 | 106.5 |
| 4 | 4 | −20 | 10.78 | 106.5 |
| 5 | 4 | −17 | 10.5 | 106.5 |
| 6 | 5 | −18 | 10.5 | 106.5 |
| 7 | 4 | −17 | 10.5 | 106.5 |
| 8 | 5 | −12 | 10.5 | 106.5 |
| 9 | 8 | −24 | 10.5 | 106.7 |
| 10 | 8 | −20 | 10.5 | 106.5 |
| 11 | 8 | −18 | 10.6 | 106.7 |
| 12 | 9 | −20 | 10.5 | 106.5 |

EXAMPLE 2

Twelve examples of self-expanding stents of size 12×60 mm were

| Settings for Experiment | |
|---|---|
| Crimp Velocity = | 32.8 mm/sec |
| Fire Size = | 1.6 mm |
| Crimp Force = | 70 Lbs |
| Stent Chill Size = | 10 mm |
| E-Tube chilling time = | 2 sec |
| Iris Chilling size = | 1.8 mm |
| E-Tube Diameter = | 6 French |

-continued

| | | Step Distance = | | 5 mm | |
|---|---|---|---|---|---|
| Stent | Number of Crimps | Average Temperature (degrees C.) | Loading Air Pressure (psi) | Stent Length When Loaded (mm) | |
| 1 | 5 | −25 | 10.19 | 62.8 | |
| 2 | 5 | −19 | 10.19 | 63 | |
| 3 | 5 | −15 | 10.49 | 62.9 | |
| 4 | 4 | −19 | 10.19 | 62.9 | |
| 5 | 4 | −19 | 10.49 | Pass through | |
| 6 | 5 | −16 | 10.49 | 62.9 | |
| 7 | 4 | −16 | 10.78 | 63 | |
| 8 | 3 | −20 | 10.19 | 63 | |
| 9 | 4 | −20 | 10.19 | 63 | |
| 10 | 3 | −23 | 10.19 | 63.2 | |
| 11 | 4 | −25 | 10.19 | 63 | |
| 12 | 4 | −25 | 10.19 | Pass through | |

EXAMPLE 3

Twelve examples of self-expanding stents of size 7×125 mm were successfully loaded into delivery devices under the following conditions.

| Settings for Experiment | |
|---|---|
| Crimp Velocity = | 32.8 mm/sec |
| Fire Size = | 1.6 mm |
| Crimp Force = | 60 Lbs |
| Stent Chill Size = | 10 mm |
| E-Tube chilling time = | 2 sec |
| Iris Chilling size = | 1.8 mm |
| E-Tube Diameter = | 6 French |
| Step Distance = | 2.5 mm |

| Stent | Number of Crimps | Average Temperature (degrees C.) | Loading Air Pressure (psi) | Stent Length When Loaded (mm) |
|---|---|---|---|---|
| 1 | 4 | −39 | 11.23 | 130 |
| 2 | 5 | −35 | 11.07 | 130 |
| 3 | 6 | −35 | 11 | 130.5 |
| 4 | 4 | −34 | 11.1 | 130 |
| 5 | 4 | −34 | 11 | 129.8 |
| 6 | 4 | −38 | 11.07 | 129.22 |
| 7 | 4 | −39 | 11 | 129.2 |
| 8 | 5 | −38.2 | 11.36 | 129.2 |
| 9 | 5 | −39.5 | 11.07 | 129.2 |
| 10 | 6 | −40 | 11.07 | 129 |
| 11 | 9 | −36 | 11.01 | 129 |
| 12 | 5 | −42 | 11.2 | 129 |

EXAMPLE 4

Twelve examples of self-expanding stents of size 8×125 mm were successfully loaded into delivery devices under the following conditions.

| Settings for Experiment | |
|---|---|
| Crimp Velocity = | 32.8 mm/sec |
| Fire Size = | 1.6 mm |
| Crimp Force = | 70 Lbs |
| Stent Chill Size = | 10 mm |
| E-Tube chilling time = | 2 sec |
| Iris Chilling size = | 1.8 mm |

-continued

| E-Tube Diameter = | | | 6 French | |
|---|---|---|---|---|
| Step Distance = | | | 5 mm | |
| Stent | Number of Crimps | Average Temperature | Loading Air Pressure (psi) | Stent Dim. When Loaded (mm) |
| 1 | 23 | −20 | 10.49 | 128.5 |
| 2 | 13 | −15 | 10.4 | 128.5 |
| 3 | 12 | −16 | 10.49 | Pass through |
| 4 | 14 | −18 | 10.49 | 128 |
| 5 | 18 | −15 | 10.49 | 128 |
| 6 | 20 | −14 | 10.49 | 128 |
| 7 | 25 | −15 | 10.49 | 128 |
| 8 | 24 | −14 | 10.49 | 128 |
| 9 | 19 | −16 | 10.49 | 128 |
| 10 | 24 | −16 | 10.49 | 128 |
| 11 | 28 | −14 | 10.49 | 128 |
| 12 | 22 | −16 | 10.49 | 128 |

Stents suitable for use in a stent loader 10 may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

In at least one embodiment, a method of loading a stent may comprise:

a) providing a crimping device having a crimping chamber constructed and arranged to reduce the diameter of a stent;

b) providing a support device to support a delivery device having an internal diameter, the support device constructed and arranged to move the delivery device with respect to the crimping device, the delivery device oriented to receive a stent from said crimping device;

c) providing a fluid source arranged to direct a fluid flow through the crimping chamber of the crimping device, the fluid being at a temperature lower than an ambient temperature;

d) providing a self-expanding stent;

e) orienting the stent within the crimping chamber of the crimping device;

f) directing said fluid flow through the crimping chamber of the crimping device;

g) reducing the size of the crimping chamber to reduce an outer diameter of the stent to less than the internal diameter of the delivery device;

h) increasing the size of the crimping chamber, wherein said fluid flow advances the stent such that at least a portion of the stent exits the crimping chamber and enters the delivery device;

i) moving the delivery device away from the crimping device, thereby moving another portion of the stent out of the crimping chamber;

j) reducing the size of the crimping chamber to reduce of a portion of the stent oriented within the crimping chamber to an outer diameter less than the internal diameter of the delivery device;

k) moving the delivery device toward the crimping device, thereby further advancing the stent into the delivery device;

l) in the event that a portion of the stent is still oriented within the crimping chamber, increasing the size of the crimping chamber and repeating steps i-k as necessary until the entire stent is oriented within the delivery device.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A method of loading a self-expanding stent comprising:

a) providing a crimping device having a crimping chamber constructed and arranged to reduce the diameter of a stent;

b) providing a support device to support a delivery device having an internal diameter, the support device constructed and arranged to move the delivery device with respect to the crimping device, the delivery device oriented to receive a stent from said crimping device;

c) providing a fluid source arranged to direct a fluid flow through the crimping chamber of the crimping device, the fluid being at a temperature lower than an ambient temperature;

d) providing a self-expanding stent;

e) orienting the stent within the crimping chamber of the crimping device;

f) directing said fluid flow through the crimping chamber of the crimping device;

g) reducing the size of the crimping chamber to reduce an outer diameter of the stent to less than the internal diameter of the delivery device;

h) increasing the size of the crimping chamber, wherein said fluid flow advances the stent such that at least a portion of the stent exits the crimping chamber and enters the delivery device;

i) moving the delivery device away from the crimping device, thereby moving another portion of the stent out of the crimping chamber;

j) reducing the size of the crimping chamber to reduce of a portion of the stent oriented within the crimping chamber to an outer diameter less than the internal diameter of the delivery device; and k) moving the delivery device toward the crimping device, thereby further advancing the stent into the delivery device.

2. The method of claim 1, further comprising increasing the size of the crimping chamber and repeating steps i-k to advance another portion of the stent into the delivery device.

3. The method of claim 1, wherein the portion of the stent that exits the crimping chamber during step h has a length that is less than a full length of the stent.

4. The method of claim 1, wherein a longitudinal axis of said crimping chamber and a longitudinal axis of said delivery device are coaxially aligned.

5. The method of claim 1, wherein said support device moves said delivery device in an axial direction.

6. The method of claim 1, wherein said support device moves with said delivery device.

7. The method of claim 1, wherein said fluid flow cools the stent to a martensitic state during prior to step h.

8. The method of claim 1, wherein said fluid flow is continuously provided throughout steps g-k.

9. The method of claim 1, wherein said fluid flow comprises a fluid cushion between the stent and the crimping chamber during step h.

10. The method of claim 1, wherein said fluid flow is in a stent axial direction.

11. The method of claim 1, wherein said fluid flows through the crimping chamber and the delivery device.

12. The method of claim 1, wherein said fluid comprises a gas.

13. The method of claim 12, wherein said fluid comprises at least one inert gas.

14. The method of claim 1, wherein a portion of the stent frictionally engages the delivery device during step h.

15. The method of claim 1, wherein the stent further comprises a coating.

16. The method of claim 15, wherein said fluid flow cools the coating to a temperature below a glass transition temperature of the coating.

17. The method of claim 1, wherein the stent has a length of at least 100 mm.

* * * * *